(12) United States Patent
Müller et al.

(10) Patent No.: US 8,758,803 B2
(45) Date of Patent: Jun. 24, 2014

(54) FILM-SHAPED PREPARATION COMPRISING OILY SUBSTANCES FOR ORAL ADMINISTRATION

(75) Inventors: Markus Müller, Troisdorf (DE); Holger Piotrowski, Weissenthurm (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 259 days.

(21) Appl. No.: 12/736,521

(22) PCT Filed: Apr. 30, 2009

(86) PCT No.: PCT/EP2009/003138
§ 371 (c)(1),
(2), (4) Date: Oct. 14, 2010

(87) PCT Pub. No.: WO2009/138170
PCT Pub. Date: Nov. 19, 2009

(65) Prior Publication Data
US 2011/0064830 A1 Mar. 17, 2011

(30) Foreign Application Priority Data
May 13, 2008 (DE) .......................... 10 2008 023 345

(51) Int. Cl.
*A61F 13/00* (2006.01)
*A61K 9/14* (2006.01)
*A61K 9/00* (2006.01)
*A61K 9/70* (2006.01)

(52) U.S. Cl.
CPC ............. *A61K 9/0056* (2013.01); *A61K 9/7007* (2013.01)
USPC ............ 424/434; 424/435; 424/484; 424/486

(58) Field of Classification Search
CPC ........ A61K 9/0056; A61K 8/89; A61K 47/34
USPC ................................. 424/434, 435, 484, 486
See application file for complete search history.

(56) References Cited

U.S. PATENT DOCUMENTS

| | | | |
|---|---|---|---|
| 3,444,858 A | 5/1969 | Russell | |
| 4,128,445 A | 12/1978 | Sturzenegger et al. | |
| 5,462,749 A * | 10/1995 | Rencher | 424/484 |
| 6,177,096 B1 | 1/2001 | Zerbe et al. | |
| 2003/0224053 A1 * | 12/2003 | Fotinos et al. | 424/486 |
| 2004/0137027 A1 | 7/2004 | Horstmann et al. | |
| 2005/0019291 A1 | 1/2005 | Zolotarsky et al. | |
| 2007/0292479 A1 * | 12/2007 | Podhaisky et al. | 424/435 |
| 2008/0233174 A1 * | 9/2008 | Myers et al. | 424/435 |

FOREIGN PATENT DOCUMENTS

| | | |
|---|---|---|
| DE | 24 49 865 | 4/1976 |
| DE | 196 52 257 | 6/1998 |
| EP | 0219762 | 10/1986 |
| EP | 0460588 | 6/1991 |
| EP | 0452446 | 12/1993 |
| WO | WO 2006/078998 | 7/2006 |

OTHER PUBLICATIONS

Dyerassi; "Steroid Contraceptives in the People's Republic of China" *New England Journal of Medicine*; vol. 289, No. 10; pp. 533-535 (1973).

* cited by examiner

*Primary Examiner* — Abigail Fisher
(74) *Attorney, Agent, or Firm* — D. Peter Hochberg; Sean F. Mellino; Richard A. Wolf

(57) ABSTRACT

Water-soluble, solid, film-shaped preparations comprising at least one film-forming polymer selected from the group consisting of the fully and partially hydrolyzed polyvinyl alcohols, and at least one water-insoluble, oily liquid which is incorporated into the film-forming polymer and amounts to at least 30 percent by weight, relative to the dry portion of the preparation. Methods for producing the preparations and the use thereof are also provided.

18 Claims, No Drawings

FILM-SHAPED PREPARATION COMPRISING OILY SUBSTANCES FOR ORAL ADMINISTRATION

CROSS-REFERENCE TO RELATED APPLICATIONS

This application is a National Stage application of International Application No. PCT/EP2009/003138, filed on Apr. 30, 2009, which claims priority of German application number 10 2008 023 345.5, filed on May 13, 2008, both of which are incorporated herein by reference in their entireties.

BACKGROUND OF THE INVENTION

1. Field of the Invention

The present invention relates to solid, film-shaped preparations comprising at least one oily substance for oral administration.

2. Description of the Prior Art

Flat-shaped forms of administration for use in the oral region and on the mucous membranes of the mouth, so-called wafers, are known. U.S. Pat. No. 3,444,858 describes medicament strips based on a gelatine-containing material. Also, medicaments in the form of films were already described at the beginning of the seventies, such as, for example, in the New England Journal of Medicine, 289, 533-535 (1973). The utility model specification DE 24 49 865 describes active pharmaceutical ingredient carriers in the form of films that contain various active ingredients and concentrations of active ingredients.

U.S. Pat. No. 4,128,445 discloses technical solutions for the loading of carrier material with active ingredients. In this connection, the patent addresses the subsequent addition of active ingredient preparations onto prefabricated film-shaped preparations. The document describes loading methods in dry and in moist form that aim at a uniform, subsequent distribution of active ingredient on a layer.

Also known are proposals for active ingredient-loaded films for applications outside the medical field. EP 0 219 762, for example, discloses a water-soluble film of starch, gelatine, glycerine or sorbite that is coated using a roll coating process. In this connection, it is stated therein that such dosage forms may also be produced utilising flavouring substances.

A formulation suited for producing film-shaped flavouring substance-containing preparations is described in EP 0 460 588. A composition of 20 to 60%-wt. film former, 2 to 40%-wt. gel former, 0.1 to 35%-wt. active ingredient or flavouring substance, and not more than 40%-wt. of an inert filler is considered to provide special advantages. Apart from other compounds, polyvinyl alcohol is mentioned as a gel former. It has, however, emerged that the gel-forming properties of polyvinyl alcohol are only to a limited extent compatible with the film formers mentioned in that printed publication. A content of 20 parts by weight, and more, of film former—mostly a sugar derivative, polyethylene glycol, or the like—resulted in a considerable loss of aroma occurring already in the drying of thin layers, which is part of the production process.

Flavouring substance-containing forms of administration for application in the oral region are also known from EP 0 452 446, but this document does not describe any measures to prevent an evaporation of flavouring substances during production and/or storage. As a solution to that problem, DE 196 52 257 discloses individually dosed, film-shaped forms of administration which rapidly disintegrate upon contact with a liquid and which can be produced avoiding loss of active ingredients during their production and storage. These film-shaped forms of administration have an internal, liposoluble phase in the form of droplets that contain the flavouring substance and are present in an outer, solid but water-soluble phase, with the outer phase comprising, relative to the water-free portions, at least 40%-wt. of polyvinyl alcohol, up to 30%-wt. of a surface-active substance and 0.1 to 30%-wt. of an internal phase, relative to the outer phase.

Film-shaped preparations for application in the mouth are already available on the market as active ingredient-containing or flavouring substance-containing forms of administration. For example, wafer-thin strips that leave a cool, breath-fresh taste sensation on the tongue without sucking or chewing are sold in the flavours "Peppermint", "Wild-Mint" and "Lemon-Frost" by the company Wrigley under the names ECLIPSE FLASH®, or by the company Pfizer in the flavours "COOL MINT®", "FRESHBURST®", Cinnamon and "Fresh Citrus" under the trade mark Listerine POCKETPAKS®.

Hydrophilic, film-forming polymers are used to achieve a rapid disintegration or rapid dissolution behaviour of film-shaped preparations on contact with saliva.

However, if oily substances are to be administered with a film-shaped preparation that rapidly dissolves in the oral cavity, the differing properties of the matrix (=hydrophilic film-forming polymer) and of the oily substance (hydrophobic) which is to be incorporated in the matrix cause problems.

Since hydrophilic polymers usually only have a low absorption capacity for lipophilic substances, the amount of oily substance with which hydrophilic films can be loaded is limited. This limitation becomes particularly apparent if larger amounts of an oily liquid are to be processed with a hydrophilic polymer into a film since in that case the oily substance exudes, for example due to phase separation occurring during the preparation of the compound (separation of the oil-in-water emulsion) or, later, during storage of the films.

However, for certain applications it is necessary to accommodate a large amount of an oily substance in a film-shaped preparation. For example, to achieve a desired therapeutic effect it may be necessary to load the film with a large amount of an oily active ingredient. For example, for the active ingredient simethicone, which is used as a carminative, a dose of about 80 mg is indicated as therapeutically effective. This amount is administered, for example, by means of known liquid forms of administration. For an administration by means of a film-shaped preparation rapidly disintegrating in the mouth, this amount would however be too large to be able to produce stable films.

To avoid the stability problems occurring during the loading of a hydrophilic film with a hydrophobic substance, surface-active substances are usually added to a material consisting of a hydrophilic polymer and a hydrophobic, liquid or oily substance, i.e. tensides or emulsifiers which reduce the interfacial surface tension between the phases. U.S. Pat. No. 6,177,096, for example, discloses the production of film-shaped forms of administration with addition of surface-active substances.

However, the use of surface-active substances in oral preparations is frequently undesirable because it can have a negative impact on the taste sensation by causing a soapy foreign taste. In addition, the amount of the surface-active substances added to the film-forming polymer limits the possible total loading of the film with oily substance if the surface-active substances do not themselves possess film-forming properties as well.

SUMMARY OF THE PRESENT INVENTION

The problem to be solved by the present invention was therefore to provide film-shaped preparations, rapidly disintegrating on contact with saliva or other aqueous liquids, that are capable of stably containing a large amount of at least one oily substance but do not comprise any additional surface-active substances.

Surprisingly, it was found that certain film-forming polymers are, even without addition of further surface-active substances, capable of stabilising larger amounts of oily substances and that stable films can be produced therefrom.

The film-forming polymers that are capable of stabilising larger amounts of at least one oily substance even without addition of further surface-active substances are fully hydrolysed polyvinyl alcohols and partially hydrolysed polyvinyl alcohols.

Polyvinyl alcohols are water-soluble polymers of vinyl alcohol. Vinyl alcohol is generally present in the tautomeric form of the acetaldehyde. For this reason, polyvinyl alcohol cannot be produced by polymerisation of its monomers but is obtained by saponification of polyvinyl acetate. To this end, polyvinyl acetate is saponified, or hydrolysed, with sodium hydroxide. The polyvinyl alcohols that have not been fully saponified with sodium hydroxide contain vinyl alcohol units and vinyl acetate units. These polyvinyl alcohols are referred to as partially hydrolysed polyvinyl alcohols.

It is known that polyvinyl alcohol increases the surface-active effect of other tensides. Its good emulsifying capacity is likewise known (cosmetics, skin film, US 2005/0019291 A1). Although the simultaneous use of polyvinyl alcohol as a film former and (possibly sole) emulsifier for the production of stable, solid films comprising an oily component for oral application is mentioned in DE 196 52 257 A1, according to indications in this printed publication the portion of the internal (oily) phase is limited to a maximum of 30% (g/g), and the portion of the film former amounts to at least 40% (g/g), in each case relative to the water-free total system.

DETAILED DESCRIPTION OF THE PRESENT INVENTION

The water-soluble, solid, film-shaped preparations of the invention, by contrast, comprise 30 to 80%-wt., preferably 40 to 60%-wt. of at least one oily substance and 5 to 70%-wt., in the preferred embodiment 5 to 60%-wt., of at least one partially hydrolysed or fully hydrolysed polyvinyl alcohol. In a preferred embodiment, the water-soluble, film-shaped preparation comprises partially hydrolysed polyvinyl alcohols, especially partially hydrolysed polyvinyl alcohols with a degree of hydrolysis of about 88%, that is, having a degree of hydrolysis of 86.7 to 88.7%.

In a particularly preferred embodiment, the partially hydrolysed polyvinyl alcohols have a degree of hydrolysis of about 88%, and a viscosity between 4 and 40 mPa·s as a 4% aqueous solution at 20° C. The polyvinyl alcohols available under the trade name MOWIOL® from Kuraray Specialities Europe GmbH, i.e. MOWIOL® 5-88, MOWIOL® 8-88, MOWIOL® 13-88, MOWIOL® 18-88, MOWIOL® 23-88, MOWIOL® 26-88 and MOWIOL® 32-88, and comparable products, may be mentioned as examples of especially preferred partially hydrolysed polyvinyl alcohols.

Oily substances herein refers to substances that are liquid at room temperature (20° C. to 23° C.) and poorly water-soluble or water-insoluble, mixtures of such substances and such substances containing components dissolved therein. Oily substances include, for example, compounds such as the fatty oils (glyceryl esters of partially unsaturated fatty acids), mineral oils (carbohydrates that have been obtained predominantly by distillation and refining from petroleum), synthetic oils (synthetically prepared oils, e.g. esters of dicarboxylic acids, silicone oils) and etherial oils (extracts of plants and parts of plants consisting in large part of terpenes, and the synthetic copies thereof).

The oily substances can be active pharmaceutical ingredients such as dimethicone or simethicone, but they may also have other functions, for example as flavouring agents.

In preferred embodiments, the oily substance is dimethicone or simethicone. Dimethicone, chemically α(trimethylsilyl)-ω-methylpoly[oxy(dimethylsilylene)], is a clear, colourless liquid that can be mixed with chloroform or ether, but is not miscible with either water or ether. Simethicone is dimethicone mixed with silicon dioxide. Both substances are active pharmaceutical ingredients that are administered perorally as antifoaming agents and can alleviate bloating and pain caused by excess gas in the gastrointestinal tract. As a medicament, simethicone is available as a chewing tablet or in liquid form. Preparation names for the medicaments available on the market are, for example, ELUGAN®, ENDO-PARACTOL®, ESPUMISAN®, IMOGAS®, LEFAX® and SIMETHICON-RATIOPHARM®.

Further oily substances that may be contained in the preparation are menthol, bitter fennel oil, peppermint oil, caraway oil.

Peppermint oil (Menthae peperitae aetheroleum) is an ethereal oil that is obtained from the peppermint plant (*Mentha piperita*). Peppermint oil is used as a carminative and is administered to treat spasms in the upper gastrointestinal tract and spasms of the bile ducts, due to its digestive and anti-bloating properties.

The main component of peppermint oil is menthol and menthone. Menthol is a monocyclic monoterpene alcohol which at 0.4 g/l is poorly soluble in water. At room temperature, menthol is a colourless, crystalline solid.

Caraway oil (Carvi aetheroleum) is an ethereal oil that is obtained from the fully ripe fruits of the caraway plant (*Carum carvi* L.). It, too, is used as a carminative.

Bitter fennel oil is an ethereal oil of German fennel (Foeniculi amari Fructus) which is obtained by steam distillation from the seeds. Bitter fennel oil is, inter alia, digestive and has a spasmolysant effect in the gastrointestinal tract.

The preparation according to the invention may consist of 5 to 70%-wt. of at least one partially or fully hydrolysed polyvinyl alcohol and of 30 to 80%-wt. of at least one oily substance. The portion of partially or fully hydrolysed polyvinyl alcohol preferably amounts to 40 to 60%-wt., and the portion of oily substance to 40 to 60%-wt.

In a preferred embodiment, the film-shaped preparation according to the invention consists of 40%-wt. of at least one partially or fully hydrolysed polyvinyl alcohol and of 60%-wt. of at least one oily substance, preferably dimethicone or simethicone, in each case relative to the dry portion.

In particularly preferred embodiments, the preparation comprises, in addition to dimethicone or simethicone, at least one ethereal oil from the group comprising peppermint oil, bitter fennel oil and caraway oil.

The invention is, however, not limited to water-soluble, solid, film-shaped preparations of at least one polyvinyl alcohol and one or more oily substances. In preferred embodiments, the film-shaped preparation may contain further hydrophilic polymers, even if with these additional polymers it is not possible to produce stable films comprising an oily substance in a large amount if only these polymers are used as the matrix material and no further surface-active substances are added.

The additional hydrophilic polymers are preferably selected from the group comprising cellulose and cellulose derivatives, polyvinyl pyrrolidones, polyethylene oxides, pullulan, hydroxypropylated tapioca starch and alginates. In a particularly preferred embodiment, the additional hydrophilic polymers are selected from the group consisting of hydroxypropyl methyl cellulose and sodium carboxymethyl cellulose.

The film-shaped preparations may contain further excipients or additives. For example, glycerine, sorbidex, sucralose, menthol and/or colourants may be added to the polymer material to prepare the film-shaped preparation.

The amounts in which the preferred components may be contained in the film-shaped preparation are summarised in Table 1:

TABLE 1

Amounts of the components contained in the preparation

| Component | Content |
| --- | --- |
| Polyvinyl alcohol (fully/partially hydrolysed) | 5-70%-wt. |
| Oily component | 30-80%-wt. |
| Hydroxypropyl methyl cellulose | 0-35%-wt. |
| Sodium carboxymethyl cellulose | 0-35%-wt. |
| Glycerine | 0-20%-wt. |
| Sorbidex | 0-20%-wt. |
| Sucralose | 0-2%-wt. |
| Menthol | 0-10%-wt. |
| Bitter fennel oil | 0-5%-wt. |
| Peppermint oil | 0-5%-wt. |
| Caraway oil | 0-5%-wt. |
| Total | 100%-wt. |

The invention also relates to methods for producing the preparations according to the invention. The preparations according to the invention can be produced by preparing a material containing at least one film-forming polymer from the group of the fully and partially hydrolysed polyvinyl alcohols and at least 30%-wt., relative to the dry portion of the preparation, of a water-insoluble, oily liquid in an aqueous solvent, preferably water. This material is then coated on a support, and the resultant coating is dried.

The film-shaped preparations which contain dimethicone, simethicone, peppermint oil, bitter fennel oil and/or caraway oil as the oily substance, can be used as carminatives as they can alleviate complaints in the region of the gastrointestinal tract, such as bloating, spasms and/or flatulence.

EXAMPLES

To examine the absorption capacity of hydrophilic, film-forming polymers for oily substances more closely, different amounts of simethicone were processed into films in combination with different polymers by initially mixing an aqueous polymer solution with simethicone. This mixture was coated on a support, and the coating was dried.

Example 1

A homogeneous material of the following composition was prepared:

| | |
| --- | --- |
| 16%-wt. | Polyvinyl alcohol (MOWIOL ® 8-88, partially hydrolysed polyvinyl alcohol, degree of hydrolysis: 85-89%, viscosity (4% in $H_2O$, 20° C.): 7-9 mPa · s) |
| 24%-wt. | Simethicone |
| 60%-wt. | Water |

Films prepared with this material remained stable.

Example 2

A homogeneous material of the following composition was prepared:

| | |
| --- | --- |
| 14%-wt. | Sodium carboxymethyl cellulose (WALOCEL ® CRT 30 GA; DS: 0.65-1.45, viscosity (2%): 20-40 mPa · s) |
| 6%-wt. | Simethicone |
| 80%-wt. | Water |

However, owing to wetting problems it was not possible to prepare coatings with this material that had no defects.

Example 3

A homogeneous material of the following composition was prepared:

| | |
| --- | --- |
| 21%-wt. | Polyvinyl pyrrolidone (KOLLIDON ® 90; K-value: 81.0-96.3) |
| 9%-wt. | Simethicone |
| 70%-wt. | Water |

Films prepared with this material exuded simethicone.

Example 4

A homogeneous material of the following composition was prepared:

| | |
| --- | --- |
| 17.5%-wt. | Polyethylene oxide (POLYOX ® WSR N80; viscosity (5%, 25° C.): 55-90 cP) |
| 7.5%-wt. | Simethicone |
| 75.0%-wt. | Water |

Films prepared with this material exuded simethicone.

Example 5

A homogeneous material of the following composition was prepared:

| | |
| --- | --- |
| 28%-wt. | Pullulan (PI-20; viscosity: 128 $mm^2/s$) |
| 12%-wt. | Simethicone |
| 60%-wt. | Water |

Owing to wetting problems, it was not possible to prepare coatings with this material that had no defects. In addition, films prepared with this material exuded simethicone.

Example 6

A homogeneous material of the following composition was prepared:

| | |
|---|---|
| 4.4%-wt. | sodium alginate (MANUCOL ® LDP MCLLDP 25BG; viscosity (1%): 4.00-15.00) |
| 6.6%-wt. | Simethicone |
| 89.0%-wt. | Water |

Films prepared with this material exuded simethicone.

Example 7

A homogeneous material of the following composition was prepared:

| | |
|---|---|
| 10.4%-wt. | Hydroxypropyl cellulose (KLUCEL ® LF; viscosity (5%): 75-150 mPa·s) |
| 15.6%-wt. | Simethicone |
| 74.0%-wt. | Water |

Films prepared with this material exuded simethicone.

As is shown by Example 1, it was possible to prepare stable films from partially hydrolysed polyvinyl alcohol which contained a portion of 60%-wt. of simethicone, relative to the dry portion. With other hydrophilic, film-forming polymers, it was not possible to prepare stable films, as is shown by the examples 2 to 8, which are to be regarded as comparative examples.

Example 8

Example of a recipe for a stable film with simethicone:

| | |
|---|---|
| 27.48%-wt. | MOWIOL ® 8-88 |
| 58.00%-wt. | Simethicone |
| 10.00%-wt. | Peppermint flavour |
| 1.00%-wt. | Sucralose |
| 2.50%-wt. | Sorbidex |
| 1.00%-wt. | Titanium dioxide |
| 0.02%-wt. | Patent blue |

Example 9

Example of a recipe for a stable film with simethicone:

| | |
|---|---|
| 26.09%-wt. | MOWIOL ® 8-88 |
| 7.00%-wt. | Pharmacoat 606 (hydroxypropyl methyl cellulose; substitution type 2910, viscosity (2%-wt. in H₂O): 4.8-7.2 mPa·s) |
| 0.50%-wt. | WALOCEL ®CRT 30 GA |
| 57.14%-wt. | Simethicone |
| 3.00%-wt. | Glycerine |
| 3.00%-wt. | Sorbidex |
| 0.35%-wt. | Sucralose |
| 0.40%-wt. | Menthol |
| 1.00%-wt. | Bitter fennel oil |

-continued

| | |
|---|---|
| 1.00%-wt. | Peppermint oil |
| 0.50%-wt. | Caraway oil |
| 0.02%-wt. | Yellow No. 6 |

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A water-soluble, solid, dried film-shaped preparation comprising at least one film-forming polymer selected from the group consisting of fully and partially hydrolysed polyvinyl alcohols, and at least one oily substance that is incorporated into the film-forming polymer in amounts to at least 50 percent by weight, said preparation containing at least one oily substance selected from the group consisting of silicone oils wherein the film-shaped preparation does not exude said at least one oily substance.

2. The preparation according to claim 1, wherein the partially hydrolysed polyvinyl alcohols are respectively selected from the group consisting of the partially hydrolysed polyvinyl alcohols having a degree of hydrolysis of about 88%.

3. The preparation according to claim 1, wherein the partially hydrolysed polyvinyl alcohols respectively have a viscosity of 4 to 40 mPa·s as a 4% aqueous solution.

4. The preparation according to claim 1, wherein said preparation further contains at least one ethereal oil selected from the group consisting of bitter fennel oil, peppermint oil and caraway oil.

5. The preparation according to claim 1, wherein said preparation comprises at least one further hydrophilic polymer.

6. The preparation according to claim 5, wherein said at least one further hydrophilic polymer is selected from the group consisting of celluloses, cellulose derivatives, polyvinyl pyrrolidones, polyethylene oxides, pullulan, hydroxypropylated tapioca starch and alginates.

7. The preparation according to claim 1, wherein said preparation comprises at least one excipient or additive.

8. The preparation according to claim 1, wherein said preparation comprises a composition according to the following table:

| Component | Content |
|---|---|
| Polyvinyl alcohol (fully/partially hydrolysed) | 5-70%-wt. |
| Oily component, as defined in claim 1 | 30-80%-wt. |
| Hydroxypropyl methyl cellulose | 0-35%-wt. |
| Sodium carboxymethyl cellulose | 0-35%-wt. |
| Glycerine | 0-20%-wt. |
| Sorbidex | 0-20%-wt. |
| Sucralose | 0-2%-wt. |
| Menthol | 0-10%-wt. |
| Bitter fennel oil | 0-5%-wt. |
| Peppermint oil | 0-5%-wt. |
| Caraway oil | 0-5%-wt. |
| Total | 100%-wt. |

9. The preparation according to claim 1, wherein said preparation contains no surface-active agents.

10. The preparation according to claim 1, wherein the at least one oily substance is selected from the group consisting of simethicone and dimethicone.

11. The preparation according to claim 1, wherein the at least one oily substance amounts to not more than 80%-wt. relative to the dry portion of the preparation.

12. The preparation according to claim 11, wherein the at least one oily substance amounts to not more than 60%-wt., relative to the dry portion of the preparation.

13. The preparation according to claim 7, wherein said at least one excipient or additive is selected from the group consisting of glycerine, sorbidex, sucralose, menthol and colourants.

14. A method for producing a preparation according to claim 1, comprising the steps of:
coating a support with a material comprising at least one fully or partially hydrolyzed polyvinyl alcohol and at least 50 percent by weight, relative to the dry portion of the preparation, of an oily substance as defined in claim 1, in an aqueous solvent, to form a coating; and
drying said coating.

15. The method according to claim 14, wherein the solvent is water.

16. The method according to claim 14, wherein said method takes place without the addition of surface-active agents.

17. The method according to claim 14, wherein said at least one oily substance is selected from the group consisting of simethicone and dimethicone.

18. A method of using the film-shaped preparation according to claim 1 as a carminative for treating complaints of the gastrointestinal tract comprising the step of administering the film-shaped preparation to an individual in need thereof.

* * * * *